(12) United States Patent
Plank

(10) Patent No.: US 6,991,456 B2
(45) Date of Patent: Jan. 31, 2006

(54) LIGHT HARDENING APPARATUS

(75) Inventor: Wolfgang Plank, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 263 days.

(21) Appl. No.: 10/288,909

(22) Filed: Nov. 6, 2002

(65) Prior Publication Data

US 2004/0053191 A1 Mar. 18, 2004

(30) Foreign Application Priority Data

Sep. 12, 2002 (DE) .............................. 102 42 366

(51) Int. Cl.
*A61C 3/00* (2006.01)

(52) U.S. Cl. .................................... 433/29; 250/504 H

(58) Field of Classification Search ................ 433/29; 606/15–16; 600/245–246; 250/504 H
See application file for complete search history.

(56) References Cited

U.S. PATENT DOCUMENTS

| | | | | |
|---|---|---|---|---|
| 4,230,453 A | * | 10/1980 | Reimers ...................... | 433/29 |
| 4,677,252 A | * | 6/1987 | Takahashi et al. .......... | 174/254 |
| 5,144,534 A | | 9/1992 | Kober | |
| 5,371,327 A | | 12/1994 | Fujinami | |
| 5,420,768 A | * | 5/1995 | Kennedy ..................... | 362/119 |
| 5,634,711 A | * | 6/1997 | Kennedy et al. ............ | 362/119 |
| 5,985,697 A | | 11/1999 | Chaney | |
| 6,068,474 A | | 5/2000 | Senn et al. | |
| 6,102,696 A | * | 8/2000 | Osterwalder et al. ......... | 433/29 |
| 6,123,545 A | | 9/2000 | Eggler et al. | |
| 6,200,134 B1 | | 3/2001 | Kovac | |
| 6,331,111 B1 | * | 12/2001 | Cao ............................ | 433/29 |
| 6,572,954 B1 | | 6/2003 | Haller | |
| 2004/0029069 A1 | * | 2/2004 | Gill et al. ..................... | 433/29 |

FOREIGN PATENT DOCUMENTS

| | | |
|---|---|---|
| DE | 40 03 344 C1 | 6/1991 |
| DE | 43 04 747 C2 | 9/1993 |
| DE | 198 15 846 A1 | 10/1999 |
| DE | 198 15 846 C2 | 10/1999 |
| DE | 199 52 246 A1 | 5/2000 |
| DE | 199 45 708 C2 | 4/2001 |
| DE | 101 27 416 A1 | 12/2002 |
| EP | 0 948 944 A1 | 10/1999 |
| JP | 10027926 | 1/1998 |
| JP | 11304967 | 11/1999 |
| JP | 2000271155 | 10/2000 |
| JP | 2001327517 | 11/2001 |
| JP | 2002036272 | 2/2002 |
| JP | 2002153423 | 5/2002 |

* cited by examiner

*Primary Examiner*—John J Wilson
(74) *Attorney, Agent, or Firm*—John C. Thompson; Alan S. Korman

(57) ABSTRACT

A light hardening apparatus for hardening light hardenable material includes a printed circuit having a carrier layer comprised of isolating material. The printed circuit is bendable and has conductor paths extending thereon or therethrough at spacings from one another. The apparatus includes a cooling body and a light source having a plurality of light emitting diode (LED) chips.

19 Claims, 5 Drawing Sheets

LIGHT HARDENING APPARATUS

CROSS-REFERENCE TO RELATED APPLICATIONS

This application claims foreign priority benefits under 35 U.S.C. §119(a)–(d) from German patent application ser. no. P 102 42 366.0 filed Sep. 12, 2002.

BACKGROUND OF THE INVENTION

The present invention relates to a light hardening apparatus for hardening a light hardenable material.

A light hardening apparatus of this type has long been conventionally known, whereby reference can be had, for example, to the light hardening apparatus disclosed in DE-PS 198 15 846. Such light hardening apparatus operate to harden light hardenable material such as, for example, material in the mouth of a patient, and are additionally deployed for hardening light polymerizable dental material. Printed circuits are available when a rapid and cost efficient configuration of a circuit needs to be realized. In the solution disclosed in DE-PS 198 15 846, a conductor plate extends vertically to the light exit device of the light source transversely through the handgrip of the light hardening apparatus. Electronic and electrical components are disposed on the printed circuit which, in part, also contribute to a power loss and, thus, operate as heat sources.

Light hardening apparatus are typically provided with heat emitting light sources. In this respect, halogen lamps or a multiple arrangement of LED chips are deployed. The heat given off by the light source is typically conducted away by a blower which is arranged in the rearward region of the extent of the pistol-shaped light hardening apparatus.

In order to be able to cool the components mounted on the handgrip of the light hardening apparatus, such as, for example, a longitudinal regulation transistor for the light source, it has been suggested to provide additional cooling air slots on the underside of the handgrip. A neighboring cooling air stream is to be flowed through such slots with the neighboring cooling air stream combining with the principal cooling stream from the blower. However, this solution has various disadvantages.

One disadvantage is that the principal cooling air stream and the neighboring cooling air stream extend substantially vertically adjacent one another. In the region in which the streams combine with one another, there occurs turbulence which significantly reduces the flow strength of the air stream.

Diversion ribs can, indeed, be deployed in order to achieve a less turbulent air stream. However, in a hand-held device, only a relatively small amount of space is available and additional air stream diversion measures would extend the configured length of the device, which is undesirable. If the longitudinal control transistor is simply mounted on the printed circuit board, the cooling effect of the neighboring air stream is significantly limited, in that the neighboring cooling air stream can only flow over the transistor with a reduced flow velocity. The possibility exists to mount a cooling device on the transistor so that the cooling efficiency is substantially improved. A cooling device of this type is comprised principally of metal and increases the weight of the light hardening apparatus, which is not desired.

The use of a solution of this type is, in any event, not possible if a light hardening apparatus having an accumulator disposed thereon, whose energy source is located in the handgrip, is to be used, as this necessitates that the entire electronic layout must be disposed in the transition region between the handgrip and the balance of the light hardening apparatus.

SUMMARY OF THE INVENTION

The present invention provides, in contrast to the prior art, a solution to the challenge of providing a light hardening apparatus which can be flexibly deployed, which provides an improved working efficiency but is, however, of only relatively small dimension.

Via the configuration of the printed circuit in the inventive bent or angled form, the entire power electronics can, surprisingly, also be disposed in the balance of the light hardening apparatus so that the principal cooling air stream flows over these components. In this regard, the neighboring cooling air stream can be completely omitted so that the above-noted problems can be avoided from the beginning. The cooling air stream can flow in a substantially non-diverted path along the balance of the light hardening apparatus from the front cooling air slot to the blower. In this regard, the cooling efficiency is improved so that a blower with comparatively reduced power can be deployed. This has the advantage that the dentist deploying the device is less disturbed by the exit of the heated air and the noise level of the blower is lowered.

In accordance with the present invention, it is particularly advantageous if the printed circuit with the electronics thereon extends adjacent the cooling body of the light source. By the extension in the axial direction of the blower air stream and, at the same time, of the light source, the required number of electronic components can be installed despite the relatively narrow place arrangement. Also, by the use of a bendable carrier layer for the printed circuit, the present invention is not limited to a single layer board. Instead, the conventionally known multi-layer technique can be deployed. In this connection, it is especially advantageous if the light source is configured with LED technology or a low voltage halogen technology. The operational voltage lies in the double-digit voltage region so that the imperviousness to leakage of the carrier layer comprised of isolating material is exceptionally reduced. This favors, on the other hand, the free design choice of the inventive printed circuit, as thin foil plates permit easier bending or kinking without leading to material degradation or, more significantly, breakage of material.

For example, the carrier layer can have a thickness of merely 0.1 mm or even 0.05 mm so that it can be designed in the region of the thickness of the guide paths.

It is to be understood that the thickness and width of the guide paths can be accommodated in a conventional manner to the operational requirements. Preferably, the thicknesses of the guide paths over the entire printed circuit are uniform in each layer and typically the flow-conducting conductors are substantially wider than the signal conductors.

It is particularly advantageous, as well, that the cooling ribs of the inventive light hardening apparatus can be deployed for conducting heat away from the heat emitting components of the electronics of the light hardening apparatus as well. The inventive cooling body, in this connection, has a double function—namely, on one hand, the cooling of the LED arrangement (or, as the case may be, the halogen glow lamp) and, as well, on the other hand, also conducting away the energy heat loss of the longitudinal regulator transistor, the thyristors or the like and this can be accomplished without imposing a demand for additional space availability in the hand grip of the light hardening apparatus.

The handgrip of the light hardening apparatus can be configured in any suitable desired manner so that the light hardening apparatus is, in its core configuration, also suitable for accumulator operation.

Due to the mounting of the heat source of the electronics on the cooling body of the light source in accordance with the present invention, a particular advantageous effect can be achieved:

In connection with reduced light strength according to the selected light hardening apparatus program of the operator, the light source emits at reduced power so that its power loss is correspondingly less. A regulation transistor, on the other hand, has, in connection with a reduced operational voltage of the light source, a relatively larger power loss. If, in the contrary situation, the regulator transistor is fully connected through, its power loss reduces relative to the multiplication product of the forward voltage and the operational flow of the light source. In contrast, in this operational condition, the light source is at its maximum performance and is subjected, therefore, to its maximum power loss. The sum of the so-produced power losses are, in this connection, less than the sum or total of the maxima, so that it is surprisingly possible, in accordance with the configuration of the blower, to design an overall reduced total heat loss operation.

Due to the bendable configuration of the printed circuit, the printed circuit conforms in a contour following manner to the profile of the cooling body so that the production and mounting thereof is exceptionally simple. Preferably, an isolation layer is provided between electronic conducting components of the printed circuit and the cooling body, which prevent the occurrence of short circuits. The printed circuit can also be adhered to the cooling body in an effective manner and it is possible, as well, to use printed circuits having soldering lugs as well as SMD technology.

In accordance with the present invention, it is particularly advantageous that the printed circuit can, in connection with an LED matrix light source, be disposed exceptionally close to the LED chips of the light source. In this connection, the LED chips can be connected to the printed circuit via bond technology. This solution has the advantage, as well, that the plastic housing of the LED chips, in which they are frequently cast, can be omitted. Instead, a cover disc such as, for example, a cover disc comprised of quartz glass, can be provided so that the reduction in working efficiency which would otherwise occur due to the use of a sealing mass around the LED chips can be prevented. Nonetheless, an encapsulated and hermetically sealed configuration of the LED matrix is made available by this approach.

Further advantages, details, and features are set forth in the hereinafter following description of the embodiment of an invention in connection with the schematic drawings.

DETAILED DESCRIPTION OF THE PREFERRED EMBODIMENT

Figure 1:
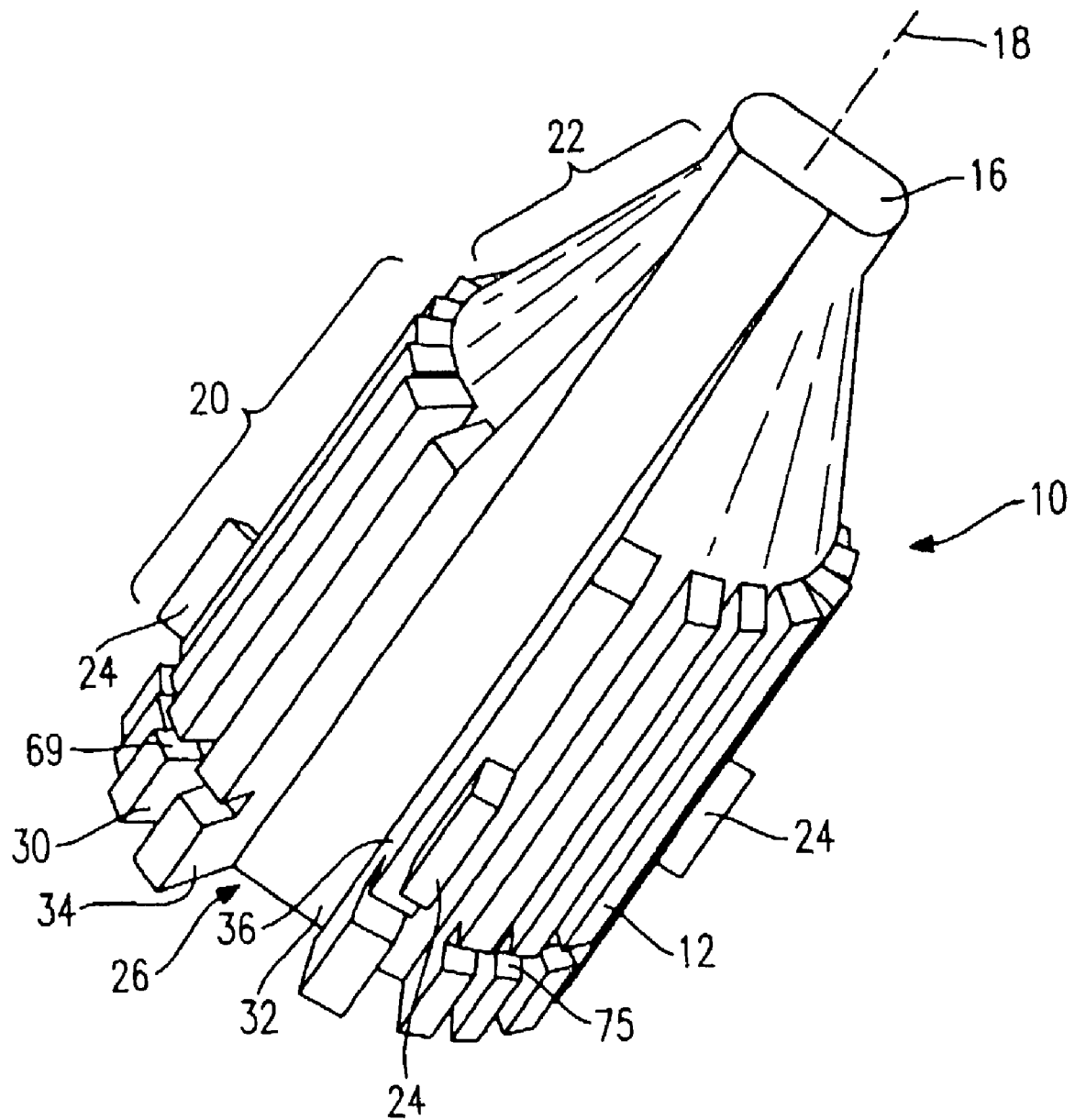
FIG. 1 is a perspective view of a cooling body for an inventive light hardening apparatus in one embodiment thereof.

As seen in FIG. 1, a first cooling body 10 is comprised as part of an inventive light hardening apparatus in one embodiment of the present invention. The cooling body 10 comprises a plurality of cooling ribs 12 which extend parallel to one another along the cooling body longitudinal axis 18. A light source 16 is disposed on the forward end of the cooling body 10, whose configuration can be best seen in FIGS. 4 and 5. The light source emits light emissions for light hardening of polymer masses along the direction, as well, of the axis 18.

The cooling body 10 comprises a rearward, substantially cylindrical region 20 and a forward conical region 22. The conical region is, in conventional manner, received along with the light source 16 in a correspondingly formed portion of a housing of the light hardening apparatus, whereby reference is had in this regard to German patent application 101 27 416, which is fully incorporated by reference herein. The cylindrical region is, in any event, received in a correspondingly formed portion of the housing. Four support elements 24 are uniformly circumferentially distributed about the circumference for fixedly supporting the cooling body 10 in the housing.

In accordance with the present invention, the cooling body 10 is provided with two opposed channels, of which a channel 26 can be seen in FIG. 1. The configuration of the opposed channel 28 is symmetrical to that of the channel 26. Each channel 26, 28 extends not only over the conical region 22 but, as well, extends over the cylindrical region 20 parallel to the axis 18 and, thus, adjacent the cooling ribs 12. While grooves 30 are configured between the cooling ribs, each of whose width is merely somewhat greater than the width of a cooling rib itself or, alternatively, corresponds to the width of a cooling rib, the channels 26 and 28 are substantially wider.

Each channel 26 and 28 is operable to receive the inventive printed circuit. In accordance with the present invention, the printed circuit can be flexible and, as well, can be comprised of multiple components, whereby it is nonetheless preferred that the printed circuit is configured as a single integral unit and has the configuration as shown in FIG. 2.

Each channel 26 and 28 includes a floor 32 and two side flanks 34 and 36, whereby the side flanks 34 and 36 diverge slightly from one another outwardly. Due to this configuration, the printed circuit can be arranged with space saving components and the printed circuit can be disposed in a channel of this configuration in a straightforward manner.

The cooling body 10 comprises, at its rear end, a blind hole-type recess 42 extending around its axis.

Figure 2:
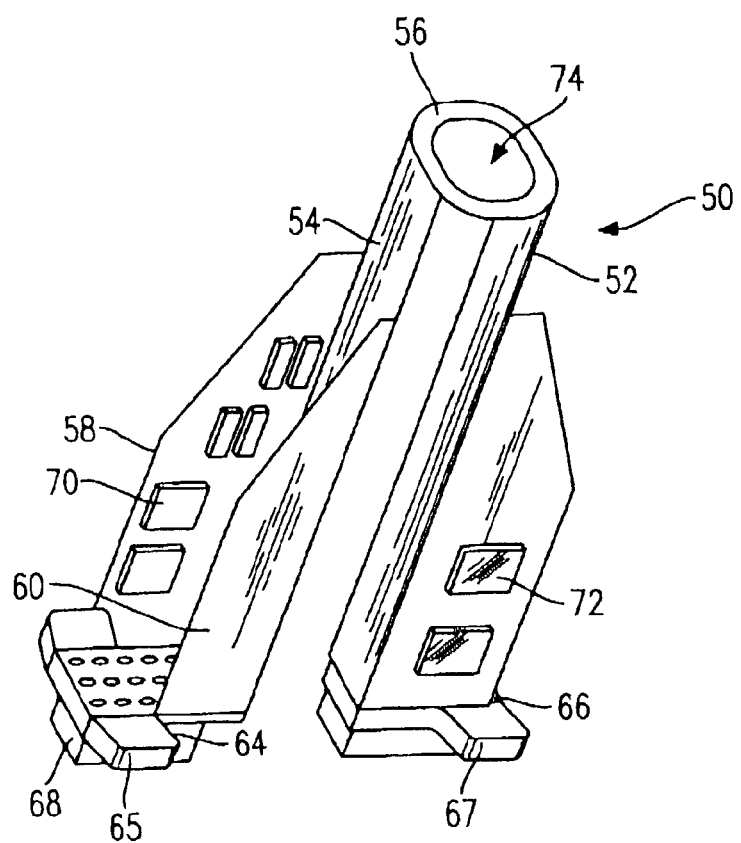
FIG. 2 is a perspective view of a printed circuit of the inventive light hardening apparatus shown in FIG. 1.

FIG. 2 shows a printed circuit 50 in an exemplary inventive embodiment. In this embodiment, the printed circuit 50 is a single integral unit, whereby it is to be understood that, instead of this configuration, it is also possible to select a multiple-component configuration and to interconnect the individual pieces of the printed circuit to one another via solder joints or, as the case may be, via plug and socket connections.

Figure 4:
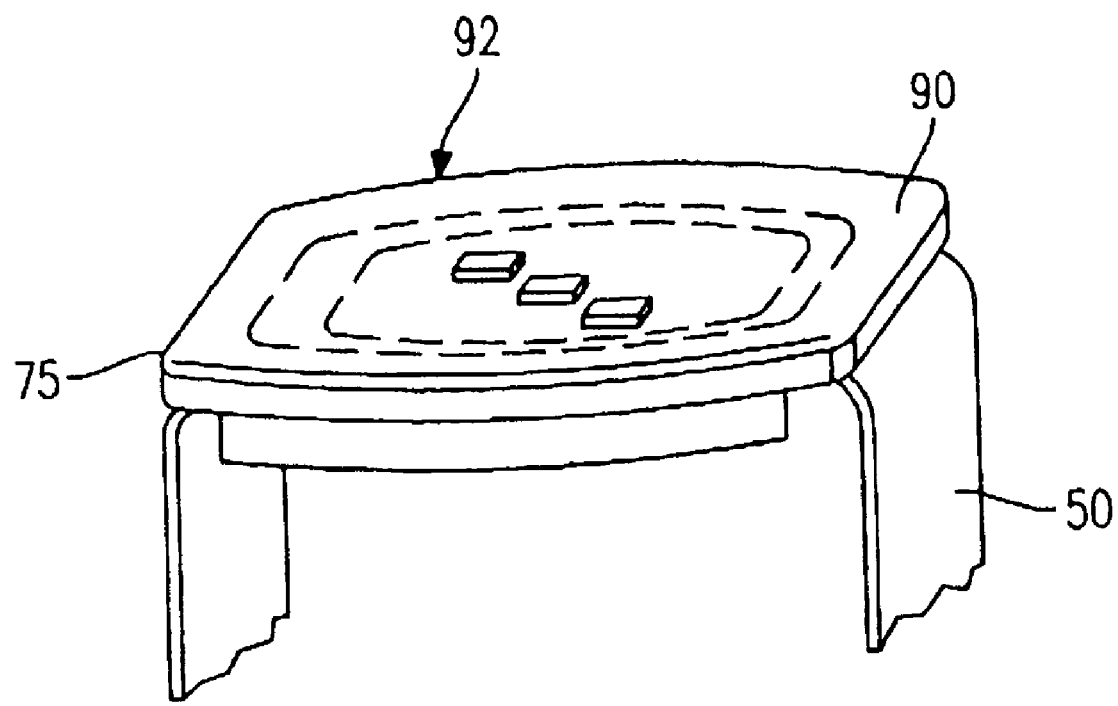
FIG. 4 is an illustration of the substrate body having the LED chips as shown in FIG. 3, whereby, additionally, a cover disc has been installed.

In accordance with the present invention, the printed circuit 50 is configured as a three-dimensional (3-D) configuration. The production of the printed circuit itself and the mounting thereon of its components occurs in the conventional manner—that is, this occurs as the printed circuit 50 still extends in planar form. By the selection of suitable bending means, the configuration of the printed circuit shown in FIG. 4 is produced. In this configuration, the printed circuit comprises two principal strips 52 and 54 which are connected to one another via a connector ring 56. Two wings 58 and 60 extend from each respective principal strip 52, 54 at an angle which corresponds to the angle of the side flanks 34 and 36 relative to the floor 32 of the channel 26.

An angled region 64, 66 is provided on the rear end of each principal strip 52, 54, respectively, with each angled region 64, 66, supporting a plug element 66, 68, respectively. Stop elements 65 and 67 are provided between the angled regions 64, 66 and the plug elements 66, 68, the stop elements operating to axially support the plug elements 66, 68. The stop elements 65, 67 extend sideways into an encircling groove 69 of the cooling body which is arranged in the rearward region of the cooling ribs. The axial length of this groove 69 substantially corresponds to the thickness of the stop elements 65, 67. In the illustrated embodiment, the printed circuit 50 is substantially configured in SMD technology, while, in the region of the plug elements 66 and 68, soldering lugs are provided.

The printed circuit 50 comprises not-illustrated conductor paths and supports numerous electrical and electronic components 70, as are schematically shown in FIG. 2. To the extent that the components are configured via SMD technology and are configured on the surfaces of the wings 58 and 60, it is also possible to provide punch outs or breakthroughs in the printed circuit and to permit the entire printed components with their cooling surfaces 72 to be sealed off in a flush manner with the underside of the printed circuit 50. This solution permits a direct cooling of the respective components via the disposition of their cooling surface 72 on the bordering cooling ribs of the cooling body 10 to be ensured.

The connector ring 56 having an axial cutout 74 interconnects the principal strips 52 and 54 with one another.

Figure 3:
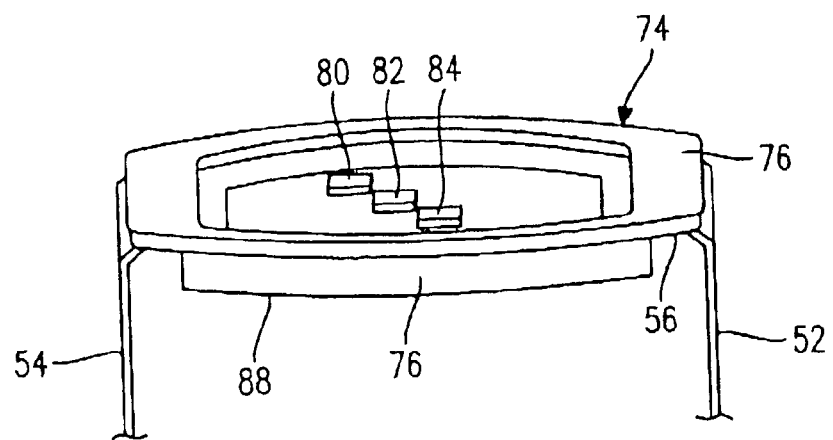
FIG. 3 is an illustration of a substrate body for receipt thereon of a light source for the light hardening apparatus shown in FIG. 1.

The configuration of the connector ring 56 for the receipt of the light source is shown in more detail in FIG. 3.

The connector ring 56 supports, on its underside, a disc-shaped substrate body 76. The substrate body 76 receives, on its upper side, a plurality of LED chips, of which three chips 80, 82, and 84 are shown. Also, in spite of the fact that only three chips are illustrated, it is to be understood that, in reality, a plurality of chips over the surface of the substrate body 76 and a matrix-type arrangement are provided.

The substrate body 76 comprises an effective heat conducting metal and has an outer shape 88 which is larger than the inner configuration of the cutout 74. The substrate body 76 is secured by adhesion to the underside of the connector ring 56 but can, however, also be secured in any other suitable manner such as, for example, by clamping.

It is to be understood that the LED chips are electronically isolated relative to the metallic substrate body 76 in conventional manner such as, for example, via a thin silicon oxide layer.

Preferably, bondable chips are used which are connected with the not-illustrated bond wires to corresponding connecting surfaces or bond pads on the printed circuit 50. In this connection, the possibility to realize substantially short bond wire length is directly due to an oval shape which is selected for the cutouts and the substrate body 76.

Figure 5:
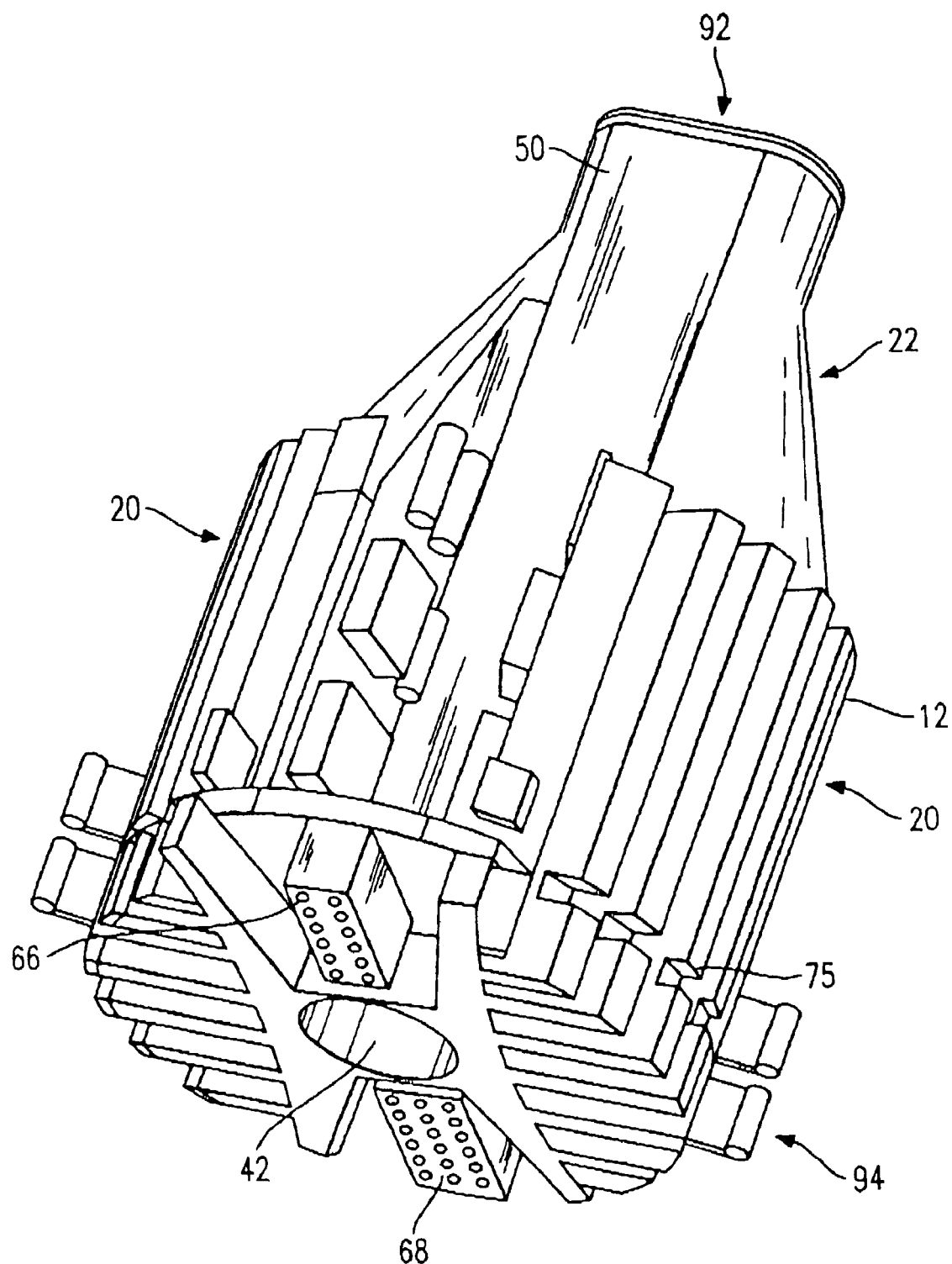
FIG. 5 is an illustration of the mounted unit comprising first and second cooling bodies, a printed circuit, and a light source for deployment in the selected embodiment of the inventive light hardening apparatus.

It is preferred to use a cover disc 90 for protecting the chips from dirt and debris, as is illustrated in FIG. 5, which can be comprised of, for example, a high transparency quartz glass. The cover disc 90 is preferably secured by adhesion on the substrate body 76 so that an enclosed unit is formed which can be, as needed, also completely changed out for an exchange unit. A not-illustrated distance ring 75 can be arranged between the forward side of the connector ring 56 and the cover disc 80 so that a spacing between the chips and the cover disc 90 can be achieved.

It is to be understood that the connection of the LED matrix, which forms the light source 92, can be disposed on the printed circuit 50 in any suitable desired manner. For example, a direct welding or soldering is possible. Alternatively, a small sister plate can be used which is insertable on the printed circuit and comprises a portion of the light source.

In accordance with the present invention, it is advantageous as well that, via the insertion of the substrate body 76 in the cutout 74, an automatically correct orientation of the light source is produced so that an after adjustment of the light source can be omitted.

A mounted unit 54 is shown in FIG. 5, which is comprised of the cooling body 10, the light source 92, and the printed circuit 50. As can be seen, the unit provides an exceptionally compact unit 94. Via the intensive through flow of the significantly deeply extending cooling ribs 12, a good cooling effect is achieved. Preferably, the grooves 30 adjacent the conical region 22 are somewhat less deep and have their maximum depth at the rearward end of the cooling body 10. In this manner, the flow velocity of the cooling air at the transition between the conical region 22 and the cylindrical region 20 is especially large and is, in the rearward region, reduced, so that there occurs a longer residence time of the cooling air on the cooling ribs 12.

Figure 6:
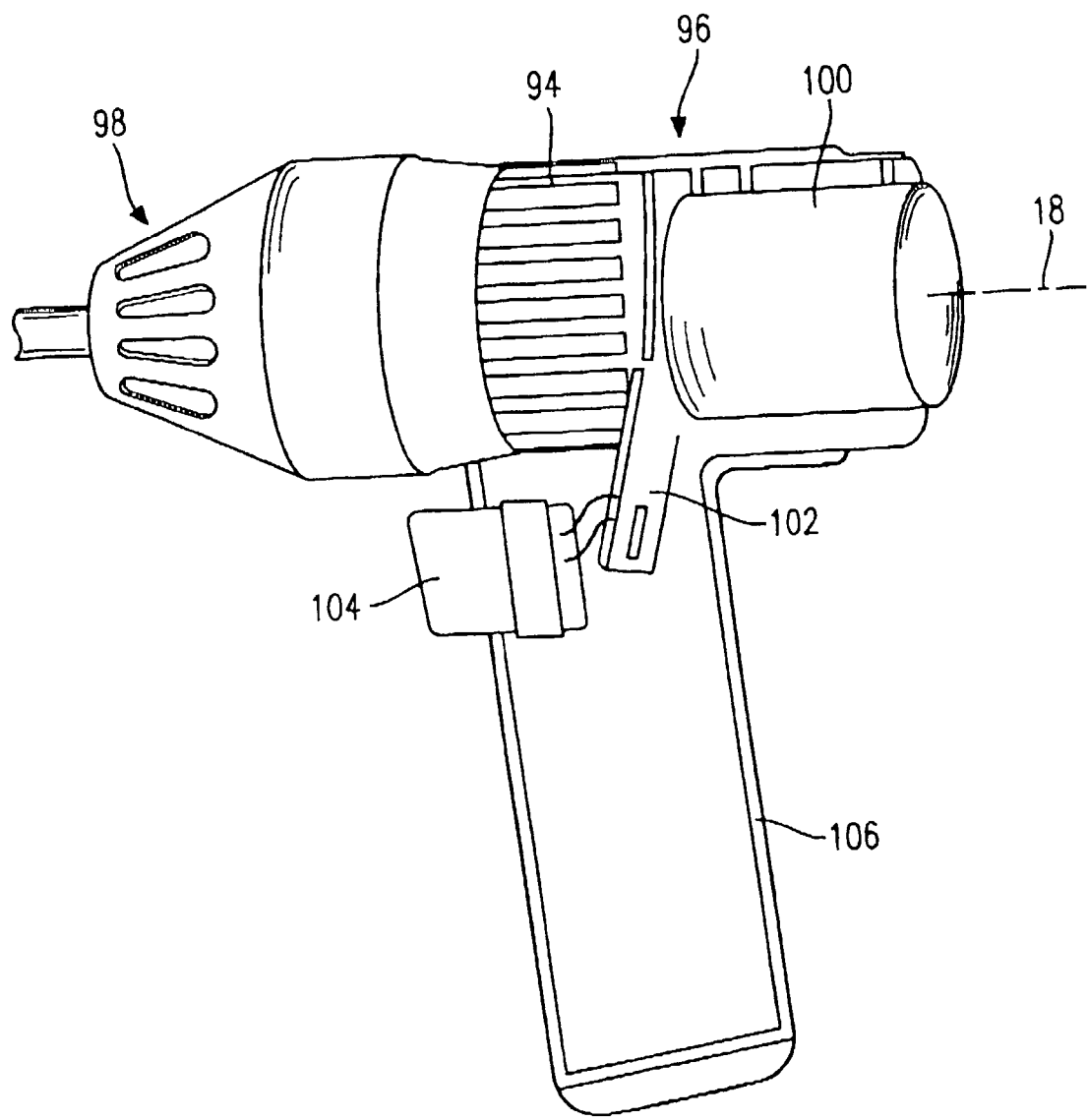
FIG. 6 is a view, in partial section, of the light hardening apparatus, whereby the mounted unit is already installed therein.

In FIG. 6, an embodiment of an inventive light hardening apparatus 96 with an installed and mounted unit 94 is illustrated. Cooling air slots 98 can be provided in conventional manner on the housing in surrounding relation to the conical region 22 which conduct the cooling air thereto. The cooling air flows along the axis 18 on the unit 94 and is exhausted outwardly by a blower 100.

As can be seen in FIG. 6, the unit 94, which has the described printed circuit which is not otherwise illustrated in FIG. 6, is connected to an additional printed circuit 102. The connection is preferably effected via bushings which correspond to the plug elements 66 and 68. The printed circuit 102 serves as the connector of the blower motor and the light source but can, however, operate as the energy source of the electronics on the printed circuit 50 and operate, as well, as the connection to a finger pressure switch 104. The energy supply can be configured either via accumulators, which are disposed in conventional manner on the hand grip 106 of the light hardening apparatus 96, or can be configured as a connector cable extending outwardly under the handgrip 106 to a base station of the light hardening apparatus 96, which ensures the electrical voltage supply.

It is to be understood that the printed circuit 102 can be configured in any suitable desired manner. It can also extend transversely through the handgrip 106 to the lower end thereof and thereat form a support position for the connector cables.

Although the herein described embodiment comprises a cooling body 10, which extends along the printed circuit 50, it is to be understood that, as needed, it is also possible without further substantial effort to configure the cooling body as a multiple-component cooling body, whereby a partition line extends, for example, along the groove.

The present invention is, of course, in no way restricted to the specific disclosure of the specification and drawings, but also encompasses any modifications within the scope of the appended claims.

What is claimed is:

1. A light hardening apparatus for hardening light hardenable material, comprising:
   a printed circuit (50), the printed circuit (50) having a carrier layer comprised of isolating material and being bendable and having conductor paths extending thereon or therethrough at spacings from one another;
   a cooling body (10), the printed circuit (50) being disposed adjacent the cooling body, the printed circuit having at least a portion bent along the cooling body (10) so that said portion lies along the longitudinal extent of the cooling body in close relationship thereto, the printed circuit being able to retain the shape to which it has been bent; and
   light source means for hardening light hardening material, the light source means being carried by the printed circuit.

2. A light hardening apparatus according to claim 1, wherein the printed circuit (50) is deformable in a selected direction about a bending radius of less than 1 centimeter.

3. A light hardening apparatus according to claim 1, wherein the printed circuit (50) is configured in a layered manner and has a thickness of between about 50 µm to 500 µm.

4. A light hardening apparatus according to claim 1, wherein the thickness of the conductor paths is greater than the thickness of the carrier layer.

5. A light hardening apparatus according to claim 1, wherein the light source means (16) has a plurality of light emitting diode (LED) chips (80, 82, 84,) the light source means (16) being mounted adjacent the rear side of the cooling body (10) and being thermally connected with the cooling body (10) and the LED chips (80, 82, 84) being electrically connected with the printed circuit (50).

6. A light hardening apparatus according to claim 1, wherein the cooling body has a plurality of cooling ribs (12) extending parallel to one another along the longitudinal extent of the cooling body and a pair of channels (26, 28) each formed between a respective adjacent pair of the cooling ribs, the printed circuit (50) being mounted at least partially in one of the two channels (26, 28).

7. A light hardening apparatus according to claim 1, wherein the cooling body has a plurality of cooling ribs (12) and a pair of channels (26, 28) each formed between a respective adjacent pair of the cooling ribs, and the printed circuit (50) is secured in the channels (26, 28) of the cooling body (10).

8. A light hardening apparatus according to claim 1, wherein the cooling body has a plurality of parallel extending cooling ribs (12), at least one pair of channels (26, 28) each formed between a respective adjacent pair of the cooling ribs, each channel (26, 28) having a base surface (32), and grooves formed between those respective adjacent pairs of cooling ribs (12) which do not have one of the channels (26, 28) therebetween, and the printed circuit (50) is thermally connected with a selected one of the base surface (32) of at least one of the channels (26, 28) and the grooves between the cooling ribs (12).

9. A light hardening apparatus according to claim 1, wherein the printed circuit (50) is bent at an end region of the cooling body (10) turned away from the light source means.

10. A light hardening apparatus according to claim 9, wherein the bent portion of the printed circuit (50) supports a plug element (24) whose plug insertion direction extends substantially parallel to the direction in which light emitted by the light source means (16) exits the light source means.

11. A light hardening apparatus according to claim 1, wherein the printed circuit (50) has a substantially U-shaped cross-section.

12. A light hardening apparatus according to claim 1, the cooling body having an extruded profile, the forward region of which has been machined or lathe turned to form a cooling conical shape.

13. A light hardening apparatus according to claim 1, further being characterized by the provision of an isolation layer drawn over the printed circuit (50) which extends to the cooling body (10) to provide electric isolation.

14. A light hardening apparatus according to claim 1, and further comprising an axial cutout (74), the printed circuit (50) having the axial cutout (74) in the region of the light source means (16).

15. A light hardening apparatus according to claim 1, and further comprising a generally disc-shaped substrate body (76), the light source means (16) having a plurality of LED chips (80, 82, 84) the LED chips (80, 82, 84) being mounted on the generally disc-shaped substrate body (76), which is thermally intensively connected to the cooling body (10), the printed circuit (50), and the LED chips (80, 82, 84).

16. A light hardening apparatus according to claim 1, wherein the light source means (16) has a plurality of LED chips (80, 82, 84) mounted on a substrate body (76) via suitable connecting wires including bond wires, the substrate body (76) being disposed between the cooling body (10) and an electrical circuit and having a transparent cover disc (90).

17. A light hardening apparatus according to claim 1, the printed circuit (50) including a power loss releasing electronic component (54) in the form of a semiconductor and comprising passive components whose cooling surfaces (72) are intensively connected thermally with the cooling body (10).

18. A light hardening apparatus according to claim 1, wherein the cooling body (10) is provided with a plug element (24), the cooling body (10) and the plug element (24) being axially spaced from one another by means of a stop element (65, 67).

19. A light hardening apparatus according to claim 1, and further comprising a light hardening apparatus (96) configured as a hand piece and including a hand grip (106), the hand grip (106) being operable to accommodate a selected one of an energy source including accumulators and a connection device for a supply cable.

* * * * *